United States Patent
Haughton et al.

(10) Patent No.: US 7,418,750 B2
(45) Date of Patent: Sep. 2, 2008

(54) PATIENT SUPPORT AND METHOD FOR STUDIES OF LUMBAR VERTEBRA ROTATION

(75) Inventors: Victor M. Haughton, Oconomowoc, WI (US); M. Elizabeth Meyerand, Cross Plains, WI (US); Baxter P. Rogers, Madison, WI (US); Ryan Henry Sydnor, Racine, WI (US); Anthony Carl Nelson, Appleton, WI (US); Jeremy Robert O'Brien, Madison, WI (US); Brian Peter Asti, Brookfield, WI (US); Rafael Davis Connemara, Milwaukee, WI (US); Michael John Hallam, Wausau, WI (US); Scott Richard Wiese, Glendale, WI (US); John Paul Puccinelli, Bayside, WI (US)

(73) Assignee: Wisconcin Alumni Research Foundation, Madison, WI (US)

( * ) Notice: Subject to any disclaimer, the term of this patent is extended or adjusted under 35 U.S.C. 154(b) by 73 days.

(21) Appl. No.: 11/489,820

(22) Filed: Jul. 20, 2006

(65) Prior Publication Data

US 2007/0033736 A1 Feb. 15, 2007

Related U.S. Application Data

(62) Division of application No. 10/377,968, filed on Feb. 28, 2003, now Pat. No. 7,127,281.

(60) Provisional application No. 60/361,422, filed on Mar. 1, 2002.

(51) Int. Cl.
A61G 7/015 (2006.01)
A61G 13/08 (2006.01)

(52) U.S. Cl. .............................. 5/601; 5/613; 378/209; 600/415

(58) Field of Classification Search ................ 5/601, 5/600, 607, 613; 600/415; 378/209
See application file for complete search history.

(56) References Cited

U.S. PATENT DOCUMENTS

| | | | | |
|---|---|---|---|---|
| 5,810,006 A | * | 9/1998 | Votruba et al. | 600/415 |
| 6,684,095 B1 | * | 1/2004 | Bonutti | 600/415 |
| 7,103,930 B1 | * | 9/2006 | Addesso-Dodd | 5/601 |
| 7,243,387 B2 | * | 7/2007 | Schindler | 5/601 |

* cited by examiner

*Primary Examiner*—Alexander Grosz
(74) *Attorney, Agent, or Firm*—Boyle Fredrickson, S.C.

(57) ABSTRACT

A patient support and software evaluate spinal instability by controlled isocentric rotation of the spine and measurement of rotation among vertebra to detect damaged vertebra having disproportionately large rotations. The patient support comprises a first support, adapted to support the shoulders of a patient, and a second rotatable support adapted to support the hips and legs of the patient.

14 Claims, 4 Drawing Sheets

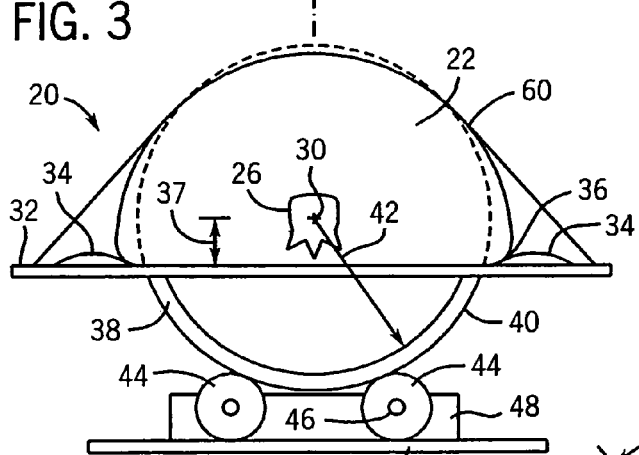
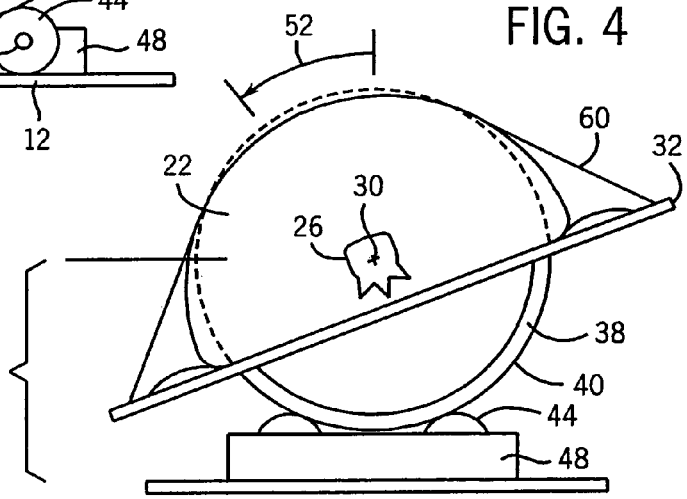
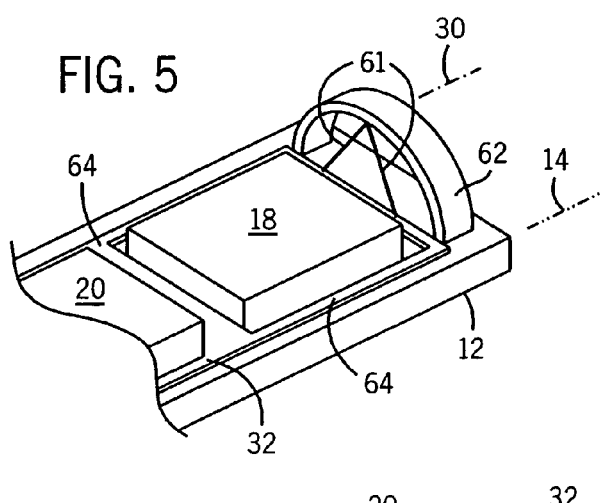
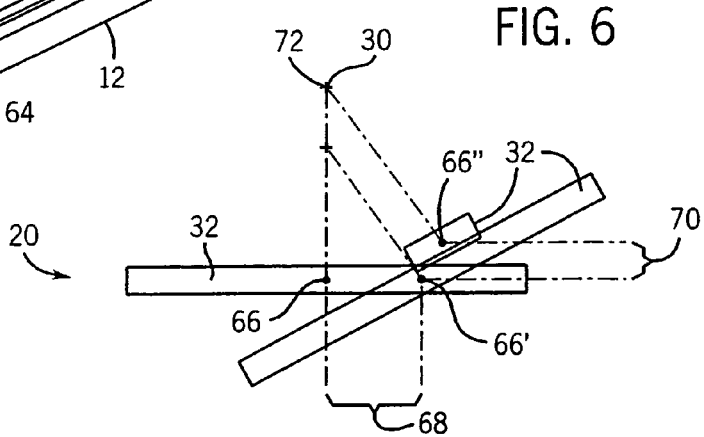

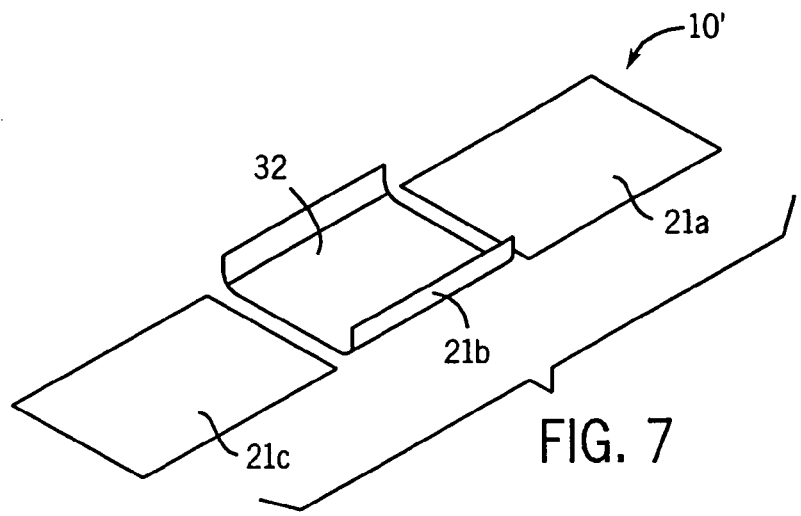
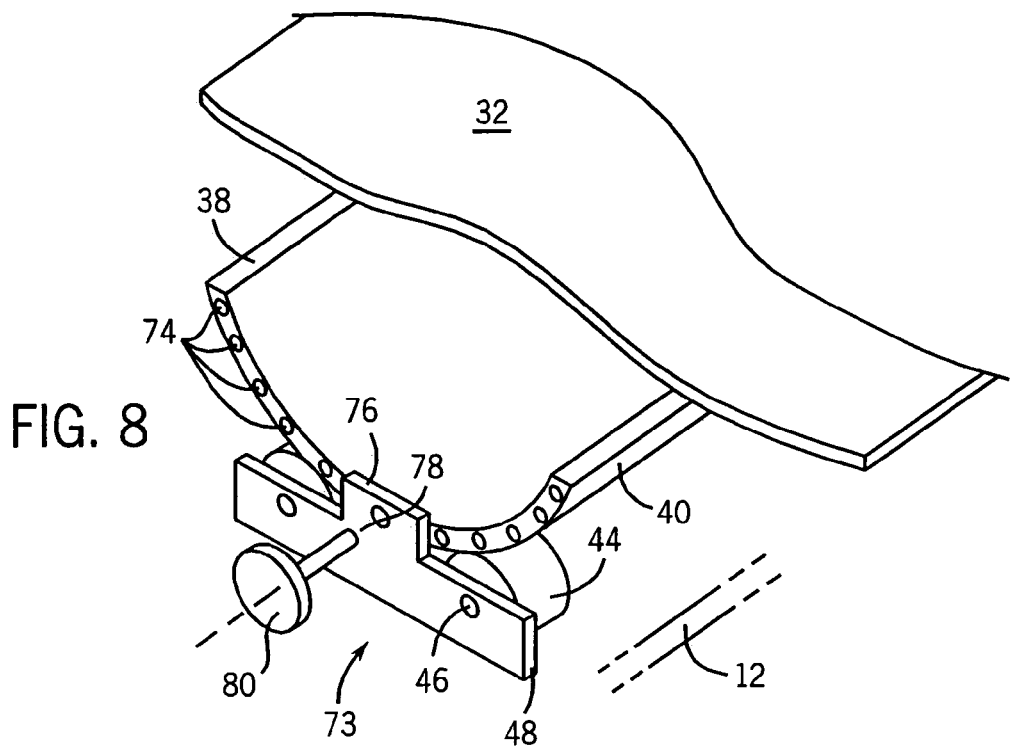
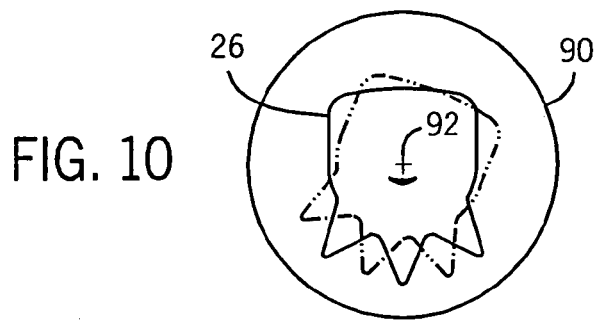

PATIENT SUPPORT AND METHOD FOR STUDIES OF LUMBAR VERTEBRA ROTATION

CROSS-REFERENCE TO RELATED APPLICATIONS

This application is a divisional of U.S. patent application Ser. No. 10/377,968, filed Feb. 28, 2003, which issued as U.S. Pat. No. 7,127,281 on Oct. 24, 2006, which claims the benefit of provisional application 60/361,422, filed Mar. 1, 2002.

STATEMENT REGARDING FEDERALLY SPONSORED RESEARCH OR DEVELOPMENT

This invention was made with United States government support awarded by the following agencies: NIH CA09206. The United States has certain rights in this invention.

BACKGROUND OF THE INVENTION

The present invention relates generally to a system for evaluating spine stability using medical imaging machines capable of producing axial tomographic or "transverse slice" images of a patient, and more generally to a patient support and software for evaluating rotation of lumbar vertebrae using such machines.

The structure of the normal lumbar intervertebral disc opposes the rotation of adjacent vertebrae in the axial plane because of the strong, obliquely oriented fibers in the annulus fibrosis in the periphery of the disk. With rupture of these fibers, secondary to a radial tear of the annulus fibrosis, the resistance to rotation in the axial plane is diminished markedly and excessive rotation can occur when a mild rotatory torque is applied to the spine. To correct this problem of hypermobility, physicians may choose to fuse the damaged vertebrae together by means of a surgical procedure eliminating the rotatory mobility and adding stability. No satisfactory means has yet been described to measure the severity of the hypermobility to determine whether it warrants this extensive surgery. Flexionextension radiographs of the spine (i.e., with the patient bending forward) have been used to detect abnormal motion of the spine in patients with back pain and suspected degenerative spinal instability. However these radiographs have poor sensitivity for hypermobility and poor specificity.

In biomechanical studies, a radial tear of the annulus fibrosis reduces the stiffness of the disc to axial rotatory forces by a factor of two or more while it affects the stiffness to flexion or extension marginally. Therefore, in theory, abnormal mobility and decreased stiffness of the lumbar spine is detected more effectively by studying the motions of the vertebra subjected to an axial rotatory torque than to a flexion or extension torque.

An invasive means to measure axial rotations of the lumbar vertebra has been described (stereophotogrammetry). In stereophotogrammetry, radio opaque markers placed on portions of the vertebrae, radiographs are obtained in two projections and then the patient is subjected to axial rotation and a second series of radiographs is obtained. Triangulation from two radiographs taken at different angles is then used to determine rotation of the vertebra. The method is too invasive and cumbersome for routine clinical use.

Another possibility has been tried recently. An open design MR magnet has been used to measure rotation of lumbar vertebra with a patient in a sitting or standing position, but without a reliable means of measurement. The type of imaging magnet which allows the patient to sit or stand is not generally available. A technique adapted to the generally available type of CT and MR scanners would be clinically more useful. The feasibility of detecting axial rotations of the lumbar spine in patients in a supine position has been documented. A study was done on supine patients in a CT machine using cushions to rotate the patient. Measurements appeared to be adequate for determination of stability, but the method was difficult to reproduce and uncomfortable for patients.

BRIEF SUMMARY OF THE INVENTION

The present invention provides an improved method for diagnosis of spinal abnormalities using axial imaging. A patient support provides rotation of one or more portions of the spine. Axial images of each vertebra are compared, before and after controlled rotation of the lumbar spine, to determine relative rotation of each vertebra. Excessive rotation may be detected. In addition, the images may be useful to identify possible spinal damage or abnormality. The invention provides a more effective means to detect and evaluate hypermobility and instability. Besides the application of the invention to the detection of abnormal motion, it may be used to demonstrate the lack of motion at some levels, thereby confirming the adequacy of a spinal fusion procedure, for example.

To this end, the present invention provides a patient support for isocentric rotation of the vertebra about the spinal axis with minimized bending of the spine about its axis. Isocentric rotation eliminates avoidable inaccuracies in the calculation of rotation study of the patient's spine using axial imaging.

Specifically, the invention provides a patient support for axial imaging studies of a patient's spine having a first support having a base adapted to be received on a table of a magnetic resonance machine and having an upper surface adapted to support a first portion of a patient. The patient support also has a rotatable support having a lower surface adapted to be received on the table of an axial imaging machine next to the first support and having an upper surface adapted to support a second portion of a patient, the rotatable support including a rotation means allowing rotating the upper surface of the rotatable support about a rotation axis substantially aligned with an axis of the patient's spine.

It is thus one object of the invention to provide rotation of the spine about the spinal axis with minimal bending of the spinal axis.

The first support may support the upper torso of the patient while the rotatable support supports the patient's hips and possibly the patient's legs.

It is thus another object of the invention to provide for rotation of the lumbar spine in particular.

The upper support may be offset below the rotation axis of the rotation means by a predetermined fixed amount equal to an average distance between a person's spine and the surface of the back. This distance averages about 10 centimeters. Therefore, in one version of the support, the center of rotation is set to be 10 cm above the surface of the support.

Thus, it is another object of the invention to provide an extremely simple coaxial rotation system recognizing that despite variations in patient size, the patient to spine to back distance is relatively constant.

The rotation means may include a bearing surface presenting a portion of a surface of a cylinder, the cylinder being coaxial about the rotation axis and a bearing support allowing rotation of the bearing surface about the rotation axis. The bearing support may be a set of rollers arranged to turn about an axis parallel to the rotation axis and upon which the bearing surface may rest.

It is thus another object of the invention to provide an extremely simple mechanism for providing coaxial rotation of the patient.

Stationary support may be separable from at least a portion of the rotatable support.

Thus, it is another object of the invention to provide a system that may be easily inserted into an MRI machine in separate portions. This separation point may be the rotation means.

The rotation means may include a means for preventing motion parallel to the axis of rotation by the rotatable support during rotation.

Further, the rotatable support and stationary support may interfit to maintain a fixed axial separation.

Thus, it is another object of the invention to prevent the stationary and rotatable portions from inadvertently separating during use by the patient The support surfaces may be padded and may include retaining straps for holding the patient to the respective support surfaces.

It is thus another object of the invention to thrive for patient comfort and safety during this procedure.

The rotation means may include a lock for holding the rotation means against rotation when in the locked mode. Thus, it is another object of the invention to provide for simplified patient positioning on the support of the present invention.

The patient support may further include and angle indicator indicating angle of the upper surface of the rotatable means with respect to one of the surface of the table and the upper surface of the stationary portion.

Thus, it is another object of the invention to provide for quantitative measurement of lumbar spine movement.

The invention provides a method of performing an axial imaging study of a patient's spine having the steps of: (1) obtaining a set of axial images of vertebrae of the spine in a first orientation of axial rotation; (2) rotating the spine axially; and (3) obtaining a second set of axial images of the vertebrae of the spine in a second orientation of axial rotation. The first and second set of axial images may be processed on an electronic computer according to a stored program to determine the relative rotation of taking place between each vertebral pair as the patient is rotated from the one position to the other. A second objective of the computer program is to display the amount of relative rotation as related to the vertebrae.

Thus, it is another object of the invention to provide an improved method of characterizing spinal instability with reduced human measurement error.

The method may also determine the relative translation of lumbar vertebrae in corresponding images of the first and second set of axial images and display the amount of relative translation as related to the vertebrae.

Thus, it is another object of the invention to provide additional, possibly clinically, important measurements of the spine movement in multiple directions and about multiple axes The summary in this application is not intended to define the scope of the invention for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

BRIEF DESCRIPTION OF THE DRAWINGS

FIG. 3 is an exaggerated cross sectional view along lines 3-3 of FIG. 1 showing the position of the patient's spine along an axis of rotation of the rotatable portion of the patient support, the axis of rotation defined by a cylindrical bearing surface movable on the rollers of the roller assemblies of FIG. 2;

FIG. 4 is an exaggerated view similar to that of FIG. 3 showing isocentric rotation of the patient's spine;

FIG. 5 is a fragmentary perspective view of an alternative mechanism for isocentric rotation of the spine using a pendulum mounting;

FIG. 6 is a simplified cross section of the rotatable portion of the patient support showing a method of providing isocentric rotation using a rotation axis displaced from the axis of the spine by combining rotation with translation of the rotation axis;

FIG. 7 is a simplified perspective view similar to that of FIG. 1 of an alternative embodiment of the invention in which a kit including stationary and rotatable patient support portions providing isocentric rotations may be combined for different procedures;

FIG. 8 is a fragmentary detail view of the cylindrical bearing surface and roller assembly of FIG. 3 showing a version of a locking mechanism for locking the rotatable portion against rotation;

FIG. 10 is an axial view of a vertebra before and after rotation using the patient support of the present invention illustrating a region of interest defined in the steps of the flow chart of FIG. 9.

DETAILED DESCRIPTION OF THE PREFERRED EMBODIMENT

Figure 1:
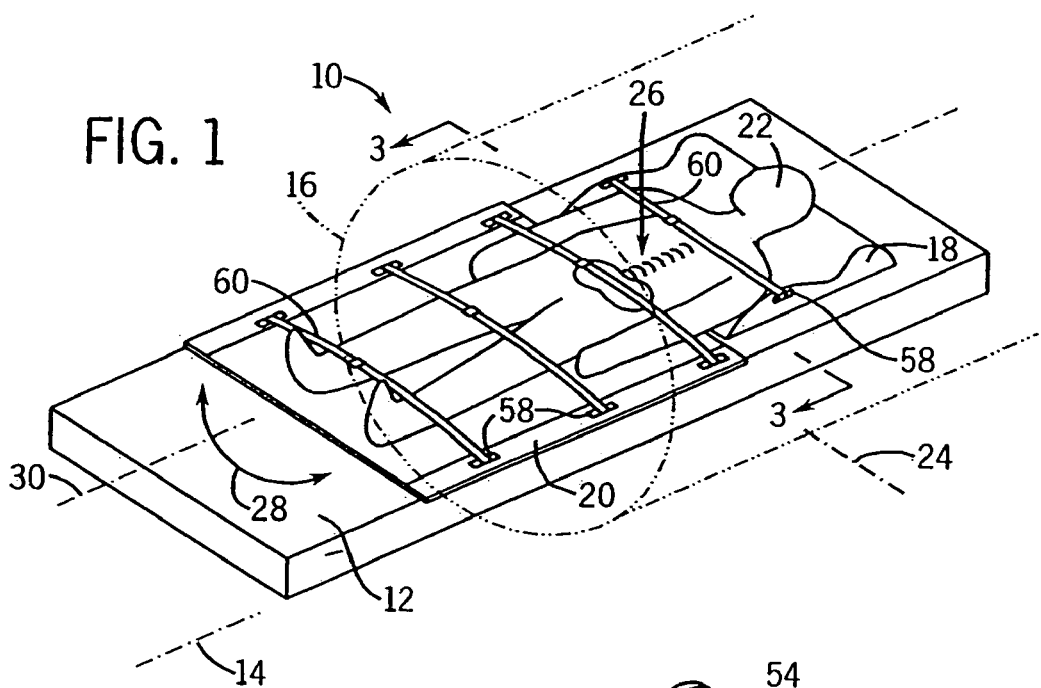
FIG. 1 is a perspective view of one embodiment of a patient support according to the present invention showing positioning of the patient's lumbar spine spanning stationary and rotatable portions of the support.

Referring now to FIG. 1, a patient support 10 of the present invention is adapted to rest on a patient table 12 and extend along a longitudinal axis 14 into a cylindrical bore 16 of an axial imaging machine. The axial imaging machine may be, for example, a computed tomography (CT) or magnetic resonance imaging (MRI) machine or other medical imaging device capable of making axial images. Axial images are those that reveal a cross-section generally perpendicular to the patient's superior-inferior axis When an MRI machine is used, it may, for example, be a GE Signa LX 1.5 T MRI scanner and the patient scanned axially with a flexible surface coil using a 3D spoiled gradient-echo (SPGR) sequence (TR=24 MS, TE=MS, 1×1×2 mm$^3$ voxels). Twenty-five scans maybe made at angular positions of 0.0-10.0° and 18.5-20.0° in 0.5° steps.

In a first embodiment, the patient support 10 includes a stationary portion 18 longitudinally adjacent to a rotatable portion 20. The stationary portion 18 and rotatable portion 20 together support a patient 22 whose shoulders and head are situated upon the stationary portion 18 and whose hips and legs are supported on the rotatable portion 20. The interface 24 between the stationary and rotatable portions 18 and 20 is positioned below lumbar vertebrae 26 of the patient. As will be described in more detail below, generally, the rotatable portion 20 may rotate 28 about an isocentric rotation axis 30 parallel to the longitudinal axis 14 and generally coaxial with an axis of the lumbar vertebrae 26.

Referring now to FIG. 3, a support plate 32 forming an upper part of the rotatable portion 20 may have padding 34 for receiving the back 36 of the patient 22. With the patient 22 supine and laterally centered on the support plate 32, a center of the lumbar vertebrae 26 of the patient 22 will be positioned substantially a fixed distance 37 of approximately ten centimeters above the center of the support plate A tube section 38 is fastened to the underside of the support plate 32 so that its outer surface 40 forms a downwardly convex surface defining a portion of a cylinder having its axis of symmetry coaxial with the center of the vertebra 26 and parallel to the longitudinal axis 14. The outer surface 40 of the tube section 38 rests upon rollers 44 that are in turn supported by axles 46 also parallel to the longitudinal axis 14. The axles 46 are held in laterally extending uprights 48 resting against the upper surface of patient table 12. The size of the tube section 38 and positioning of the rollers 44 is such as to allow a 16° rotational half range 52 to promote relative rotation between individual vertebrae of the lumbar vertebrae 26.

Referring now to FIG. 4, rotation of the support plate 32 by rolling of the rollers 44 against the outer surface 40 of the tube section 38 will cause rotation of the support plate about an isocentric rotation axis 30 centered within the vertebrae 26. This supported isocentric rotation allows rotation of the vertebrae 26 to occur without substantial translation of the vertebra 26 away from the isocentric rotation axis 30 or twisting of the vertebral axes away from parallel with the longitudinal axis 14.

Figure 2:
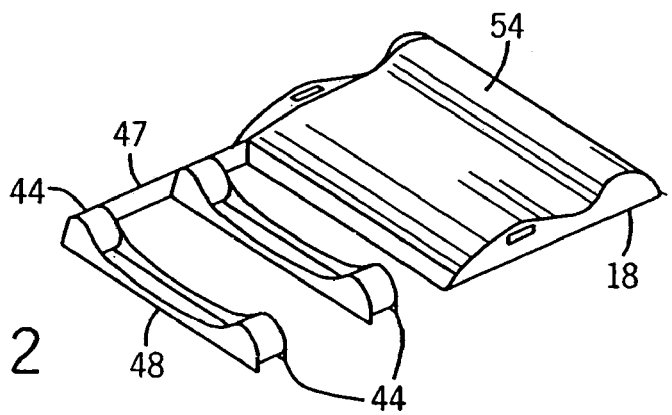
FIG. 2 is a fragmentary perspective view of the stationary portion and a lower part of the rotatable portion of the embodiment of FIG. 1 showing roller assemblies of that lower part as positioned on the patient table.

Returning again to FIGS. 1 and 2, the rollers 44 and the supporting uprights 48 may be placed on the patient table 12 independent on the remainder of the rotatable portion 20 so as to reduce the amount of weight that must be lifted onto the patient table 12 at one time. After the rollers 44 are in position, the remainder of the rotatable portion 20 including the support plate 32 and tube section 38 may then be placed on the rollers 44. In an alternative design, the rollers 44 and uprights 48 maybe connected together with spaced bars 47 and may, in fact, be attached to stationary portion 18.

Stationary portion 18 may be placed on the patient table 12 before or after the rotatable portion 20. The stationary portion 18 also includes padded surfaces 54 for patient comfort and to raise the patient comparable to that provided by the padding 34 on the rotatable portion 20. The height of the stationary portion 18 and the rotatable portion 20 may be adjusted such that the lumbar vertebrae 26 are positioned generally along a single axis.

Sides of the support plate 32 of the rotatable portion 20 may include handgrip holes 58 supporting retaining straps 60 for holding the patient 22 in place. Likewise, on the stationary support, handgrip holes 58 may support retaining straps 60 that may be positioned about the patient's chest.

Referring now to FIG. 5, it will be recognized that other mechanisms may be used to provide for the desired isocentric rotation of the vertebra 26. For example, support plate 32 of the rotatable portion 20 may be suspended by tensile members such as cords 61 at a point along isocentric rotation axis 30. The cords 61 may be held above the support plate 32 by hanger 62 in turn resting on the patient table 12. So that the cords 61 do not interfere with positioning of the patient, the hanger 62 and cords 61 may be offset along the longitudinal axis 14 just beyond the stationary portion 18 and connected by cantilever arms 64 (passing to the sides of the stationary portion 18) to connect to the rotatable portion 20. A similar hanger and cords 61 and 62 (not shown) may be placed near the patient's feet.

Referring now to FIG. 6, an actual pivot point on the isocentric rotation axis 30 is not required but can be simulated by a combination of an offset pivot point 66 with at least one of a corresponding lateral translation 68 and elevational translation 70. Thus, a spine vertebrae centered at location 72 above support plate 32 in a horizontal position may be rotated by a combination of rotation and lateral translation (indicated by pivot point 66') and/or elevation (indicated by pivot point 66"). A good approximation of isocentric rotation may be obtained with rotation and lateral translation only.

Referring now to FIG. 7, it will be understood that isocentric rotation may be provided in a patient system 10' having a number of adjacent support sections 21 a, 21 b, and 21 c that may form either rotatable portions 20 or stationary portions 18. In a two part patient support 10' having two rotating support sections 21a and 21b separated over the lumbar vertebrae, counter rotation of the upper torso and hips may be obtained. This use of two rotating support sections reduces the total angular motion required of either support sections 21 a or 21b.

Alternatively, in a three-part table, support sections 21a and 21c may be stationary with support sections 21b rotating only. Sides of the support plate 32 of the rotating support section 21b may be elevated to provide cradling of the patient 22. This configuration allows for a shortened rotation mechanism.

Other permutations are also available including rotating support sections 21c and 21b and stationary support sections 21 a. The interface between the support sections 21 may be placed along other vertebral regions including those of the cervical spine. More generally, the patient support 10' may be offered in kit form so that stationary and rotating support sections 21 may be assembled as desired according to a particular procedure. Each of the sections 21 may have a lock to hold it to adjacent sections 21 when assembled on the patient table.

Referring now to FIG. 8 and FIG. 3, the rotatable portions 20 may be provided with a locking mechanism 73. In one example locking mechanism, the end of the tube section 38 may have a series of axial holes 74 placed at regular angular intervals about the tube rim. The uprights 48 holding the rollers 44 may be extended upward to provide a tab 76 overlapping at least some of the axial holes 74 and having a hole 78 within the tab aligned at individual axial holes 74 for given rotations of the rotatable portions 20. A peg 80 may be inserted through hole 78 to engage one of the holes 74 to lock the rotatable portion 20 in a particular angular position with respect to the patient table 12. This locking may be done to assist as the patient mounts and dismounts from the patient support 10 and to holding the patient in a particular position for the image acquisitions.

Figure 9:
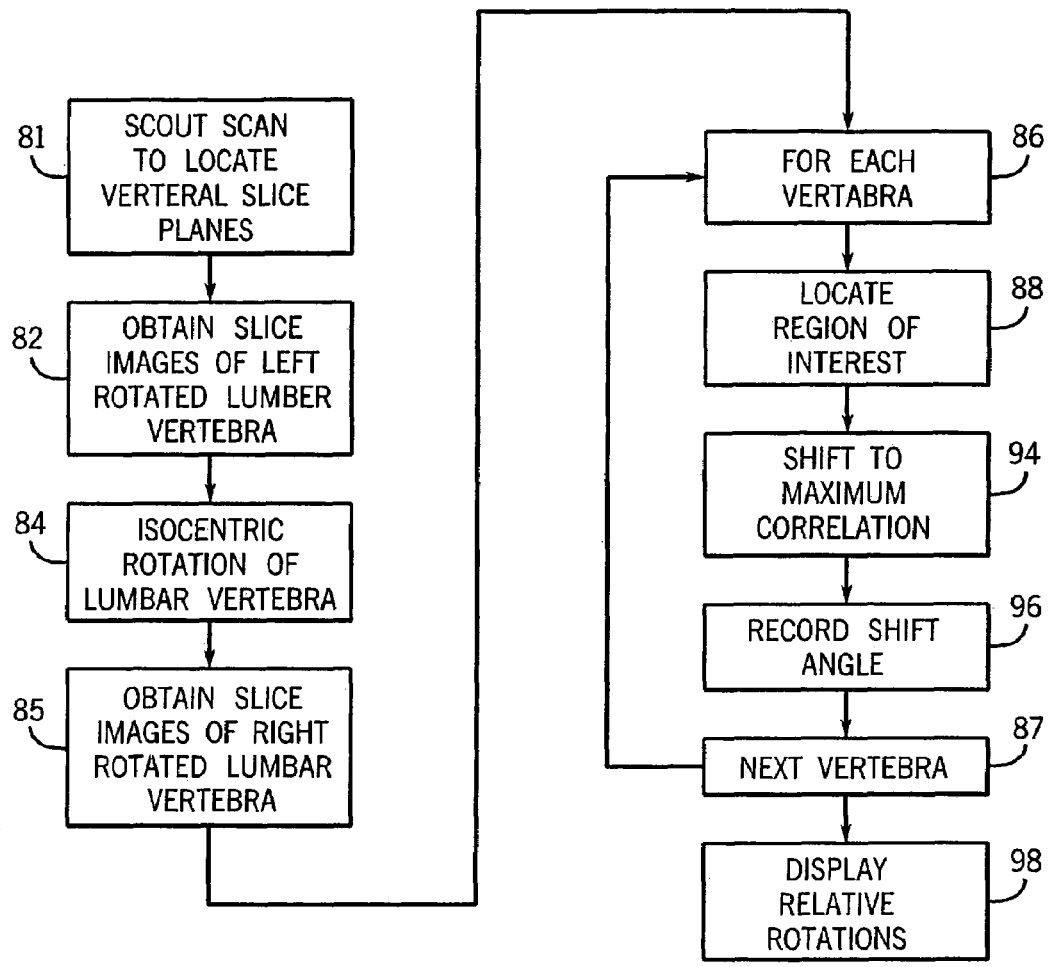
FIG. 9 is a flow chart of the steps of using the patient support of the previous figures in analyzing vertebral health.

Referring now to FIG. 9, the patient support 10 in any of the embodiments described above, may be used to evaluate spinal stability using axial imaging. In the event that the patient support 10 is used for magnetic resonance imaging, it must be constructed of non-ferromagnetic, non-conductive materials. In the event that the patient support 10 is used for computed tomography scanning, it must be constructed of radio translucent materials. Readily available commercial plastics satisfy both of these requirements.

At the start of the spinal evaluation process, the patient is placed on the patient support 10. In the preferred embodiment, the patient support of FIG. 7 having two counter rotating sections is used with shoulders on one section and hips on the other.

As indicated by process block 81, a scout scan may be taken providing an image that looks like a conventional anterior-posterior radiograph to locate the vertebra of the lumbar spine. Slice locations are identified, defining axial planes centered within each vertebra, by manual cursor placement according to methods well known in the art.

At process block 82, axial images are obtained of each vertebra in its first rotated position with the subjects' hips rotated 8° left and the shoulders were rotated 8° right, with the spine remaining isocentric with the axis of rotation.

At succeeding process block 84, the rotatable portion 20 is unlocked and rotated, for example, with the subjects' hips rotated 8° right and the shoulders rotated 8° left, with the spine remaining isocentric with the axis of rotation. In a healthy spine, these sixteen degrees of rotation will be shared by rotation of each of the vertebra of the spine equally. Damaged vertebra will show by increased relative rotation with respect to their neighbors.

At process block 86, axial images are obtained for each of the rotated vertebra. Generally the axial images of both the rotated and unrotated vertebra will be available in digitized form according to standard operation of commercially available axial imaging systems.

The images are then processed by an interactive computer program executed either on the computer system of the axial imaging system or a stand-alone computer receiving the appropriate data files. The program automatically and accurately determines the rotation of each vertebra 26 by comparison of its rotated and unrelated image per a loop represented by process blocks 86 and 87.

Specifically, per process block 88, for each image of the pair of images showing left and right rotation, a point 92 may be manually selected to use as the center of rotation. This point 92 is generally located in the midline at the dorsal edge of the vertebral body 26, selecting, as nearly as possible, the same point relative to the anatomy in each image. Alternatively, this process may be automated centering the bone of the image, for example, into a circle of like size or similar techniques known in the art.

In a first embodiment, a region of interest (ROI) 90 is defined as a circle with a radius of 37 mm about this point 92 to include as much of the vertebra 26 as possible without including substantial amounts of soft tissue. Alternatively, a circular region 49 mm in radius may be used. This larger region includes the entirety of the transverse and spinous processes of the vertebra 26 as well as some surrounding soft tissue. The ROI 90 eliminates extraneous tissue to a large degree such as may hamper accurate determination of the rotation of the vertebra 26 by automatic techniques. The ROI 90 also reduces the amount of data that must be processed.

After smoothing the images with a 21-neighbor median filter within these circular windows, the centers of rotation are aligned and one image is registered to its mate using Powell's direction set method (See. e.g., Press W H, Teukolsy S A, Vettering W T, Flannery B P. Numerical recipes in C. 2nd ed. New York: Cambridge University Press; 1992. p 412.) to maximize a measure of the correlation:

$$C = \frac{\sum (I_1 - \bar{I}_1)(I_2 - \bar{I}_2)}{\sqrt{\sum (I_1 - \bar{I}_1)^2} \sqrt{\sum (I_2 - \bar{I}_2)^2}}$$

where $I_2$ and $I_2$ are the pixel intensities of the floating and reference images, respectively; the bar denotes the mean; and the calculations are over all pixels within the circular region. See, Penney G P, Weese J, Little J A, Desmedt P, Hill DLG, Hawkes D J. *A comparison of similarity measures for use in 2-D-3-D medical image registration.* IEEE Trans Med Imaging 1998;17:586-595.

Maximizing the correlation provided the values of translation and rotation that best aligned the two images. Bilinear interpolation was used.

At process block 94, the data of two ROIs 90 for unrotated and rotated images of a given vertebra 26 are correlated with different degrees of rotation and translation (within predefined ranges) until a translation and rotation producing the greatest correlation in the values of corresponding pixels of the images is determined. Such correlation techniques are well known in the field of digital subtraction angiography and, in fact, such angiography routines may be used for this purpose modified to provide output of rotation amounts.

Generally, the correlation process compares each pixel of the image and finds a relative translation and rotation of the images that minimizes the differences between all corresponding pixels over the entire region of interest. Non-overlapping portions of the regions of interest 90 are not considered in the correlation process so that the exact placement of the regions of interest 90 previously selected manually do not affect the correlation process. The isocentric rotation of the vertebra 26 improves the accuracy of this correlation process by preventing distortion of the vertebral cross-sections with rotation such as might be caused by out-of-plane rotation of the vertebra 26.

At process block 96, the amount of angular displacement necessary for maximum correlation is recorded.

When process blocks 88, 94, and 96 have been executed for each vertebra, a graph is displayed showing the amount of rotation of each vertebra, as a function of the vertebral order, output at process block 98. Relative translation of the vertebrae may also be displayed in similar fashion.

Figure 11:
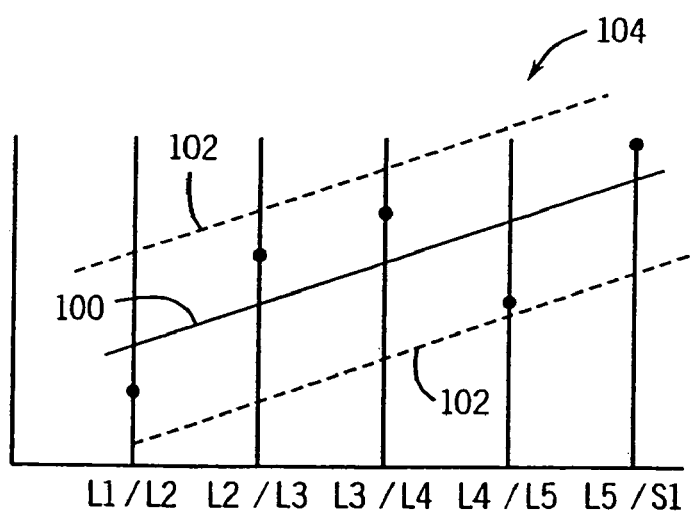
FIG. 11 is a display of the data determined by the steps of FIG. 9 showing vertebral rotations for a healthy vertebra and the potential use of this display in identifying injured or abnormal vertebra.

Referring now to FIG. 11, the output of process block 98 may provide a graph 104 indicating the rotation in absolute terms at interfaces of adjacent vertebra 26. For a healthy spine, this cumulative rotation increases approximately linearly as indicated by line 100 because of the sharing of the total rotation of the lumbar spine among vertebra. Bands 102 on either side of line 100 but parallel to that line may be determined empirically for the range or deviation from linear to be expected for normal vertebra. Readings outside of this band may be flagged automatically or visually to indicate possible damage of the material between the vertebra 26.

It will be understood from this description that the isocentric rotation of the spine may also be performed with the patient in a sitting up position, for example, in an open frame MRI system or the like, by configuring the patient support 10 to be supported vertically against the patient table 12. Further, the determination of rotation can be done three-dimensionally (e.g., as yaw, pitch and roll) to provide additional diagnostic information about the spine.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A patient support for axial imaging studies of a patient's spine comprising:
    a first support having a lower surface adapted to be received on a table of a magnetic resonance machine and having an upper surface adapted to support a first portion of a patient; and
    a rotatable support having a lower surface adapted to be received on the table of an axial imaging machine next to the first support and having an upper surface adapted to support a second portion of a patient, the rotatable support including a rotation means allowing rotating the upper surface of the rotatable support about a rotation axis substantially aligned with an axis of the patient's spine;
    wherein the upper surface of the first support is sized and arranged to support the shoulders of the patient and the upper surface of the rotatable support is sized and arranged to support the patient's hips whereby rotation of the rotatable support rotates the patient's lumbar vertebra.

2. The patient support of claim 1 wherein the upper surface of the rotatable support is sized and arranged to support the patient's hips and legs whereby rotation of the rotatable support rotates the patient's hips and legs together.

3. The patient support of claim 1 wherein the upper surface of the rotatable support is offset below the rotation axis of the rotation means by a predetermined fixed amount equal to an average distance between a person's spine and back.

4. The patient support of claim 3 wherein the predetermined fixed amount is substantially 10 cm.

5. The patient support of claim 1 wherein the rotation means includes a bearing surface presenting a portion of a surface of a cylinder, the cylinder being coaxial about the rotation axis, and a bearing support allowing rotation of the bearing surface about the rotation axis.

6. The patient support of claim 5 wherein the bearing support is a set of rollers arranged to turn about axes parallel to the rotation axis and upon which the bearing surfaces rest.

7. The patient support of claim 1 wherein the first support is separable from at least a portion of the rotatable support.

8. The patient support of claim 1 wherein the rotation means includes means for preventing axial movement of the rotatable support with respect to the first support during rotation.

9. The patient support of claim 1 wherein rotatable support and first support interfit to remain in fixed axial relationship.

10. The patient support of claim 1 wherein the upper surfaces of the stationary and rotatable portions are padded.

11. The patient support of claim 1 wherein the stationary and rotatable portions include retaining straps for holding the patient to the respective upper surfaces.

12. The patient support of claim 1 wherein the rotation means allows a rotation of from 10 to 20 degrees.

13. The patient support of claim 1 wherein the rotation means includes a lock holding the rotatable means against rotation.

14. The patient support of claim 1 including an angle indicator indicating an angle of the upper surface of the rotatable means with respect to one of the surface of the table and the upper surface of the first portion.

* * * * *

UNITED STATES PATENT AND TRADEMARK OFFICE
CERTIFICATE OF CORRECTION

PATENT NO.        : 7,418,750 B2
APPLICATION NO.   : 11/489820
DATED             : September 2, 2008
INVENTOR(S)       : Victor M. Haughton et al.

It is certified that error appears in the above-identified patent and that said Letters Patent is hereby corrected as shown below:

IN THE SPECIFICATION

Col. 8, line 8         Replace "$I_2$ and $I_2$" with --$I_1$ and $I_2$--.

Signed and Sealed this

Twenty-second Day of December, 2009

David J. Kappos
*Director of the United States Patent and Trademark Office*